United States Patent
Adachi

(10) Patent No.: US 9,310,348 B2
(45) Date of Patent: Apr. 12, 2016

(54) SUBMERGENCE DETECTING DEVICE

(71) Applicant: DENSO CORPORATION, Kariya, Aichi-pref. (JP)

(72) Inventor: Yoshiki Adachi, Okazaki (JP)

(73) Assignee: DENSO CORPORATION, Kariya (JP)

(*) Notice: Subject to any disclaimer, the term of this patent is extended or adjusted under 35 U.S.C. 154(b) by 0 days.

(21) Appl. No.: 13/758,404

(22) Filed: Feb. 4, 2013

(65) Prior Publication Data
US 2013/0214802 A1    Aug. 22, 2013

(30) Foreign Application Priority Data

Feb. 21, 2012  (JP) ................................. 2012-035425

(51) Int. Cl.
| | |
|---|---|
| *B60Q 1/00* | (2006.01) |
| *G08B 21/00* | (2006.01) |
| *G01N 33/18* | (2006.01) |
| *G01M 3/16* | (2006.01) |

(52) U.S. Cl.
CPC ............. *G01N 33/1886* (2013.01); *G01M 3/16* (2013.01)

(58) Field of Classification Search
CPC ............ G08B 21/00; B60Q 1/00; G01V 3/20; G01V 1/52; G01V 3/00; G01V 3/083; G01V 3/12; G01N 27/223; G01N 27/048; B63G 8/001; B63G 8/08; G01B 21/042; G01B 21/045
USPC ......... 324/363, 347, 358, 444, 447–449, 515, 324/634, 640, 643, 664, 689, 694; 114/257, 114/50, 331, 330; 73/314, 1.79, 116.08
See application file for complete search history.

(56) References Cited

U.S. PATENT DOCUMENTS

| | | | | |
|---|---|---|---|---|
| 4,068,221 A | * | 1/1978 | McClintock ........... | G08B 21/20 324/696 |
| 6,333,685 B1 | * | 12/2001 | Miyake ................. | B60J 7/0573 340/425.5 |

(Continued)

FOREIGN PATENT DOCUMENTS

| | | |
|---|---|---|
| JP | UM-S55-097445 A | 12/1978 |
| JP | H06-307968 A | 11/1994 |

(Continued)

OTHER PUBLICATIONS

Endo et al., Jul. 2002, Japan, A.*

(Continued)

*Primary Examiner* — Patrick Assouad
*Assistant Examiner* — Taqi Nasir
(74) *Attorney, Agent, or Firm* — Oliff PLC

(57) ABSTRACT

The submergence detecting device includes a submergence detecting terminal and a submergence judging device. The submergence detecting terminal is composed of at least two conductive sections disposed within a case. The submergence detecting terminal detects a submergence state by coming into contact with water that has infiltrated a predetermined area within the case. The submergence judging device is disposed within the case. At least a signal related to submergence detection is inputted into the submergence judging device from the submergence detecting terminal. The submergence judging device then judges whether or not submergence has occurred. The submergence detecting terminal is disposed in a position away from the submergence judging device in the downward direction.

6 Claims, 7 Drawing Sheets

(56) References Cited

U.S. PATENT DOCUMENTS

| | | | |
|---|---|---|---|
| 6,337,550 B1 * | 1/2002 | Takahashi | B60J 1/17 318/286 |
| 6,603,319 B1 | 8/2003 | Kasahara et al. | |
| 6,690,096 B2 * | 2/2004 | Sasaki | G05B 9/02 307/10.1 |

FOREIGN PATENT DOCUMENTS

| | | | | |
|---|---|---|---|---|
| JP | 2002-013963 A | 1/2002 | | |
| JP | 2002-013964 A | 1/2002 | | |
| JP | 2002-188977 A | 7/2002 | | |
| JP | 2002188977 A | * 7/2002 | | G01M 3/16 |
| JP | 2008-208648 A | 9/2008 | | |
| JP | A-2011-107096 | 6/2011 | | |

OTHER PUBLICATIONS

Dec. 23, 2014 Office Action issued in CN Application No. 201310020706.

Sep. 1, 2015 Office Action issued in Japanese Patent Application No. 2012-035425.

* cited by examiner

SUBMERGENCE DETECTING DEVICE

CROSS-REFERENCE TO RELATED APPLICATION

This application is based on and claims the benefit of priority from earlier Japanese Patent Application No. 2012-35425 filed Feb. 21, 2012, the description of which is incorporated herein by reference.

BACKGROUND OF THE INVENTION

1. Technical Field of the Invention

The present invention relates to a submergence detecting device that detects a submergence state to protect electronic components.

2. Description of the Related Art

For example, JP-A-2011-107096 is known as a conventional technology. A water intrusion detection sensor described in JP-A-2011-107096 includes a flat block-shaped insulating base placed within a container and a sensor section maintained by an insulating pressing member on a side surface of the base. The sensor section has a structure in which a plurality of sheets are layered. The sensor section is composed of a base sheet, electrode sheets bonded to both surfaces of the base sheet, and protective sheets bonded to the outer surface of the electrode sheets. Four sensor sections are respectively disposed on the four sides of the base. When water placed on an inspection surface on the top surface of the base increases and spreads to the four sides, thereby coming into contact with a sensor section, the water intrusion detection sensor detects that the sensor section is being exposed to water by detecting a difference in voltage change.

In an instance in which water has infiltrated the container, the water intrusion detection sensor is not structured to detect water infiltration some time prior to water infiltration of an electronic component to be protected. Therefore, the water intrusion detection sensor may not be capable of ensuring the safety of the electronic component before the electronic component is exposed to water.

Therefore, a submergence detecting device is desired that is capable of detecting a water infiltration state from a position away from an component to be protected from submergence, and ensuring the safety of the electronic component.

SUMMARY

As a typical example, the present application provides a submergence detecting device including a submergence detecting terminal and a submergence judging device. The submergence detecting terminal is composed of at least two conductive sections disposed within a case. The submergence detecting terminal detects a submergence state at predetermined area within the case. The submergence judging device is disposed within the case. At least a signal related to submergence detection is inputted into the submergence judging device from the submergence detecting terminal. The submergence judging device then judges whether or not submergence has occurred. The submergence detecting terminal is disposed in a position away from the submergence judging device in the downward direction (first aspect of the submergence detecting device).

According to the configuration, the submergence detecting terminal comes into contact with a fluid (such as water or an electrolytic solution) having conductivity, in a position away from the submergence judging device in the downward direction. The submergence detecting terminal thereby detects infiltration of the conductive fluid. The conductive fluid that has infiltrated the case collects in the bottom portion within the case, and water infiltration occurs. However, the submergence detecting device is capable of detecting the water infiltration state at an early stage before the submergence judging device becomes submerged. When water infiltration is detected by the submergence detecting device, the submergence judging device can be immediately protected from submergence. Therefore, the water infiltration state can be detected at a position away from the submergence judging device. In addition, safety of electronic components can be ensured before the electronic components are submerged in water.

Here, the submergence detecting terminal has at least three conductive sections. The conductive sections are made such that the lowest position of one of the conductive sections is disposed higher up than that of other conductive sections (second aspect of the submergence detecting device).

According to the configuration, the lower end of at least one conductive section, within the submergence detecting terminal having at least three conductive sections, is positioned above the lower ends of the other conductive sections. Therefore, the one conductive section is submerged later than the other conductive sections. As a result, the conductive section positioned above detects the conductive fluid after the other conductive sections have detected the conductive fluid. Therefore, the submergence detecting terminal can detect the submergence state in a plurality of stages. Thus, advancement of the submergence state can be known in stages. A submergence detecting device can be provided that is capable of allowing measures suitable for the known submergence state to be taken.

In addition, a fluid guiding section is provided in a bottom portion within the case. The fluid guiding section guides the fluid which has been infiltrated into the case to an area directly below the submergence detecting terminal (third aspect of the submergence detecting device).

According to the configuration, the fluid that has infiltrated the case is guided to an area directly below the submergence detecting terminal by way of the fluid guiding section. As a result, the submergence state can be detected while the amount of infiltrating fluid is small. Submergence at an early stage can be detected, and early-stage measures can be taken. In addition, the submergence detecting terminal detects the collected fluid. Therefore, the submergence state can be detected with certainty.

In addition, a resin member is included in a portion of the submergence detecting terminal. The resin member covers and insulates the submergence detecting terminal (fourth aspect of the submergence detecting device). According to the configuration, detection position for the conductive fluid can be set to an arbitrary height.

DETAILED DESCRIPTION OF THE PREFERRED EMBODIMENTS

A plurality of embodiments of the present invention will hereinafter be described with reference to the drawings. Sections in each embodiment corresponding to matters described in preceding embodiments are given the same reference numbers. Redundant descriptions may be omitted. When only a portion of a configuration is described in an embodiment, other embodiments described earlier can be applied to the remaining portions of the configuration. In addition to combinations of sections clearly and specifically stated as being able to be combined in each embodiment, embodiments may be combined in part even when not clearly stated as such, so long as no particular issues arise due to the combination.

First Embodiment

A first embodiment of the present invention will be described with reference to FIG. 1 to FIG. 4. A battery pack 1 according to the first embodiment includes a submergence detecting device 5 and an assembled battery. The assembled battery is composed of a plurality of single cells 10. The submergence detecting device 5 includes a submergence judging device that is mounted on a control board 50. The submergence judging device judges whether or not submergence has occurred. The submergence detecting device 5 is mounted in the battery pack 1 and quickly detects a submerged state with certainty, to protect components such as the plurality of single cells 10 from water. In the present application, the word "water" detected by the submergence detecting device 5 means, for example, water, an aqueous solution, or other various solutions including an electrolyte, being used to collectively refer to conductive fluids. The battery pack 1 can be used in, for example, a hybrid car or an electric car. The hybrid cars run by both an internal combustion engine and a motor driven by power charged in said battery.

Figure 1:
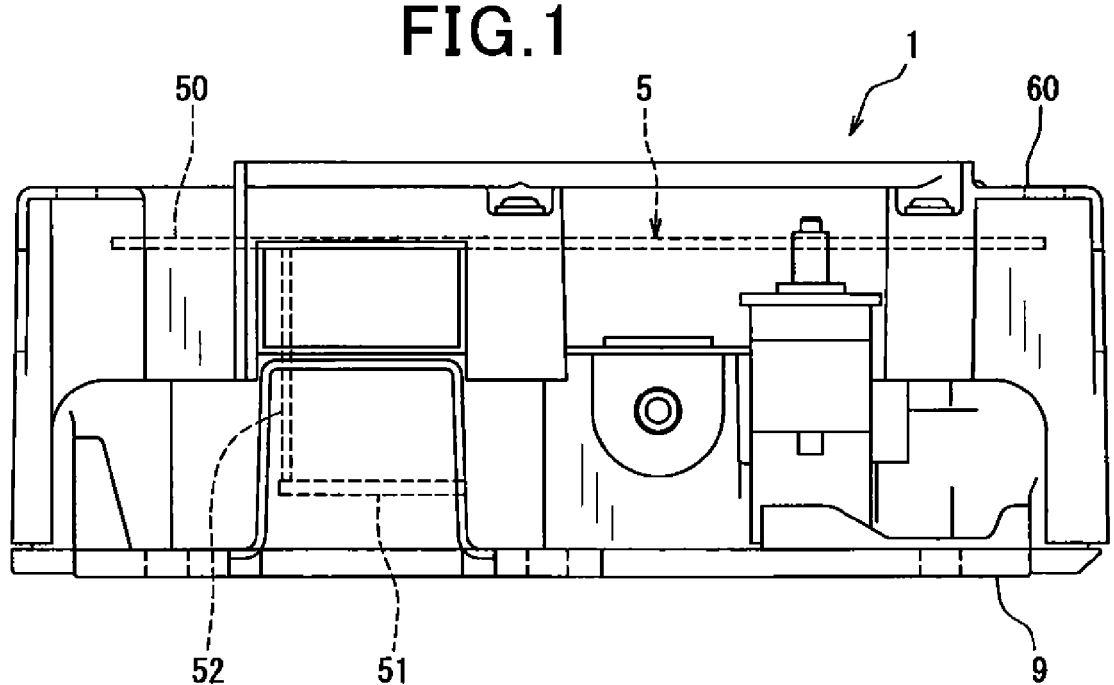
FIG. 1 is a side view of a battery pack including a submergence detecting device according to a first embodiment.

As shown in FIG. 1, the battery pack 1 is protected from the outside by a case including a base 9 and a cover 60. The plurality of single cells 10, the submergence detecting device 5, and the like are provided within the case. The submergence detecting device 5 includes the control board 50, a sensor board 51, and a communication line 52. A submergence sensor is mounted on the sensor board 51.

The base 9 supports a battery case 7 from below. The battery case 7 supports the assembled battery on which the control board 50 is placed and fixed, and the like. The base 9 includes a fixing section and an attaching section. The fixing section fixes the base 9 to the vehicle-side by bolting or the like. The attaching section attaches the cover 60 that covers the assembled battery and the like from above. The cover 60 covers the base 9 on which the main components are fixed.

The assembly is then packaged. As a result, the assembly is mounted on a vehicle as the battery pack 1. The base 9 is an aluminum member including a means for ensuring insulation from the assembled battery. The base 9 may be formed by a synthetic resin such as polypropylene (PP) or PP containing a filler or talc to improve strength.

The plurality of single cells 10 have an exterior package configuring an exterior shell, such as an aluminum can. Each single cell 10 has an electrode terminal composed of a positive terminal and a negative terminal that project from one end surface of the exterior package having a cuboid shape. The assembled battery includes a plurality of bus bars connecting between the electrode terminals such as to serially connect the plurality of single cells 10.

For example, the assembled battery is composed of five single cells 10. The battery pack is used in, for example, a hybrid car or an electric car. The running drive source of the hybrid car is a combination of an internal combustion engine and a motor driven by power charged in a battery. The running drive source of the electric car is a motor. A secondary cell configuring the assembled battery is, for example, a nickel/metal hydride secondary battery, a lithium-ion battery, or an organic radical battery. The assembled battery is disposed under a seat of the vehicle, in the space between the rear seat and the trunk compartment, in the space between the driver's seat and the passenger seat, or the like, in a state housed within a case.

Each of the five single cells 10 is housed in a predetermined position within the battery case 7, thereby integrally configuring the assembled battery. The five single cells 10 configuring the assembled battery form a plurality of first layer-built cell groups 2 and second layer-built cell groups 3. The first layer-built cell group 2 and the second layer-built cell group 3 are formed by the single cells 10 being layered in the thickness direction of the exterior package having a cuboid shape. The first layer-built cell group 2 is configured by three single cells 10 layered in the thickness direction with a predetermined gap therebetween. The second layer-built cell group 3 is configured by two single cells 10 layered in the thickness direction with a predetermined gap therebetween. In other words, the first layer-built cell group 2 and the second layer-built cell group 3 are formed by the plurality of single cells 10 being layered such that surfaces having the largest surface area, among the plurality of surfaces forming the cuboid shape, face each other. The thickness direction is also the layering direction of the layer-built cell group. In other words, the first layer-built cell group 2 and the second layer-built cell group 3 are cell groups composed of a plurality of single cells 10 layered to be flat.

All single cells 10 configuring the assembled battery are electrically connected in series via the bus bars such that the current flows in a serpentine manner. The negative terminal of a single cell 10 positioned on one end of the first layer-built cell group 2 is conductively connected to a bus bar 20. Furthermore, the bus bar 20 is connected to the vehicle-side by a screw or the like. As a result, the negative terminal is connected to the ground of the vehicle. The positive terminal of a single cell 10 positioned on the other end of the second layer-built cell group 3 is conductively connected to a bus bar 21. Furthermore, the bus bar 21 is connected to the control board 50 by a screw, welding, or the like. As a result, the positive terminal is electrically connected to the control board 50.

A safety valve is provided in the exterior package of each single cell 10. Each safety valve is positioned between the positive terminal and the negative terminal. The safety valve is set such as to break when the internal pressure of the single cell 10 becomes abnormal. The safety valve is configured by, for example, a hole opened on the end surface of the exterior package of the single cell 10 being sealed by a thin metal film adhered over the hole. In this instance, when the internal pressure of the single cell 10 becomes abnormal, the metal film breaks and the hole in the exterior package opens. Gas within the single cell 10 is discharged outside of the exterior package. As a result, cell inner pressure decreases. The single cell 10 itself is prevented from rupturing.

An insulating cover 8 insulates between the bus bars and the exterior package of the single cells 10. The insulating cover 8 is provided such as to cover an end surface portion of the exterior package, excluding at least the safety valve and the electrode terminal. In other words, when the insulating cover 8 is mounted such as to cover the end surface of the exterior package, an opening portion is formed in the insulating cover 8 that is larger than the safety valve in the position corresponding to the safety valve. In addition, an opening portion is formed in the insulating cover 8 that is larger than the electrode terminal in the position corresponding to the electrode terminal. Therefore, when the insulating cover 8 is mounted on the assembled battery that is housed within the battery case 7 and integrated, each safety valve and each electrode terminal are on the inner side of each opening portion and exposed without being covered by the insulating cover 8.

When the plurality of electrode terminals to be connected are connected by the plurality of bus bars, first, each single cell 10 is housed such as to be set in predetermined positions in the battery case 7. Next, the insulating cover 8 is mounted on the battery case 7 in which the single cells 10 are housed. At this time, the upper portion and the lower portion of the battery case 7 and the insulating cover 8 are fastened by two clips. The left- and right-side portions are fastened by two clips. Next, predetermined bus bars corresponding to six recessing portions of the insulating cover 8 integrally assembled with the battery cover 7 and the single cells 10 are fitted into the recessing portions. In this state, predetermined corresponding electrode terminals are inserted into the opening portion of each bus bar. Furthermore, each bus bar and each electrode terminal are joined by welding, such as laser welding or arc welding.

Among the plurality of first layer-built cell groups 2 and second layer-built cell groups 3, the second layer-built cell group 3 is configured to have a smaller number of layers than the adjacent first layer-built cell group 2. The second layer-built cell group 3 has a layer height amounting to two single cells 10. The first layer-built cell group 2 has a layer height amounting to three single cells 10. In this way, the first layer-built cell group 2 and the second layer-built cell group 3 form a stepped space 4 as a result of the difference in the number of layers. In this instance, the stepped space 4 forms a step equivalent to the thickness of one single cell 10.

The control board 50 is disposed in the stepped space 4. The control board 50 detects the state of the plurality of single cells 10. Therefore, the height in the thickness direction of the assembled battery including the control board 50 can be kept low. The control board 50 is placed on a boss erected in a portion of the battery case 7 housing the single cells 10 and is fixed by a screw.

The assembled battery includes a smoke discharging duct 6 that is provided such as to expose all safety valves to a smoke discharging path 6a within the assembled battery. The smoke discharging duct 6 is formed by a material having heat resistance, such as polyphenylene sulfide resin (PPS), polyethylene resin (PE), or various resins to which a fire retardant has been added. The heat resistance capability of the smoke discharging duct 6 is such that, even the pressure within the single cell 10 becomes abnormally high and the gas within the single cell 10 bursts as a result of the safety valve breaking, the duct portion does not melt and become damaged. The insulating cover 8 has insulating properties and is formed by a synthetic resin, such as polypropylene (PP resin) or PP resin containing a filler or talc. Furthermore, the insulating cover 8 is preferably formed by resin having heat resistance similar to that of the smoke discharging duct 6.

The smoke discharging duct 6 is a cylindrical body that extends in the horizontal direction. The smoke discharging duct 6 includes an opening portion that is larger than the safety valve in the positions corresponding to all safety valves when assembled to the insulating cover 8. The peripheral edge portion of the opening portion comes into close contact with the surface of the exterior package surrounding the safety valve with a gasket therebetween when assembled to the insulating cover 8. Furthermore, the smoke discharging duct 6 includes a leading duct section 6b that communicates with the smoke discharging path 6a and forms an internal path extending outwards from the side portion. The leading duct section 6b provides a function for discharging the gas that has burst into the smoke discharging path 6a outside away from the assembled battery.

The control board 50 is electrically connected to both a voltage detecting terminal 40 and the bus bar 21. An end portion of the bus bar 21 extending to the control board 50 side or to the stepped space 4 side is shaped into three terminals that project upwards. The three terminals are electrically connected to a predetermined area of the control board 50. The voltage detecting terminal 40 that projects upwards in the stepped space 4 is also electrically connected to the control board 50 disposed in the stepped space 4. A detection signal from a voltage detecting sensor that measures a predetermined electric potential of the assembled battery is outputted to the voltage detecting terminal 40. The detection signal is then outputted to the control board 50.

A battery monitoring device is a battery electronic control unit (ECU) that monitors the state of the assembled battery. The battery monitoring device is mounted on, for example, the control board 50. The battery monitoring device is connected to the assembled battery via a plurality of detection lines to detect information related to the state of the assembled battery. The detection lines extend from a detection terminal set in a predetermined position in the assembled battery. The detection line is, for example, a communication line for transmitting information, such as the voltage and temperature of the assembled battery, to the battery monitoring device. The detection terminal is a voltage measuring element, a temperature senor, or various other sensors that detect information related to the state of the assembled battery.

In addition, the battery pack 1 has electronic components that perform charging, discharging, battery temperature monitoring, and the like of the plurality of single cells 10. For example, the electronic components are various electronic components 50a and various electronic control devices. The various electronic components 50a are, for example, a DC/DC converter, an inverter, the submergence judging device mounted on the control board 50, and a power device. The battery pack 1 includes the submergence detecting device 5, the battery monitoring device, a battery control device, and a wire harness. Detection results from various sensors that monitor the state of the battery, such as voltage and temperature, are inputted into the battery monitoring device. The battery control device is configured to be capable of communicating with the battery monitoring device. The battery control device controls charge and discharge of the single cells 10 by controlling reception of power by the DC/DC converter and the like, and controls drive of a motor of an air-blowing device and the like. The wire harness connects each device. The battery pack 1 may also include an air-blowing device for cooling each single cell 10 by blowing air.

Figure 2:
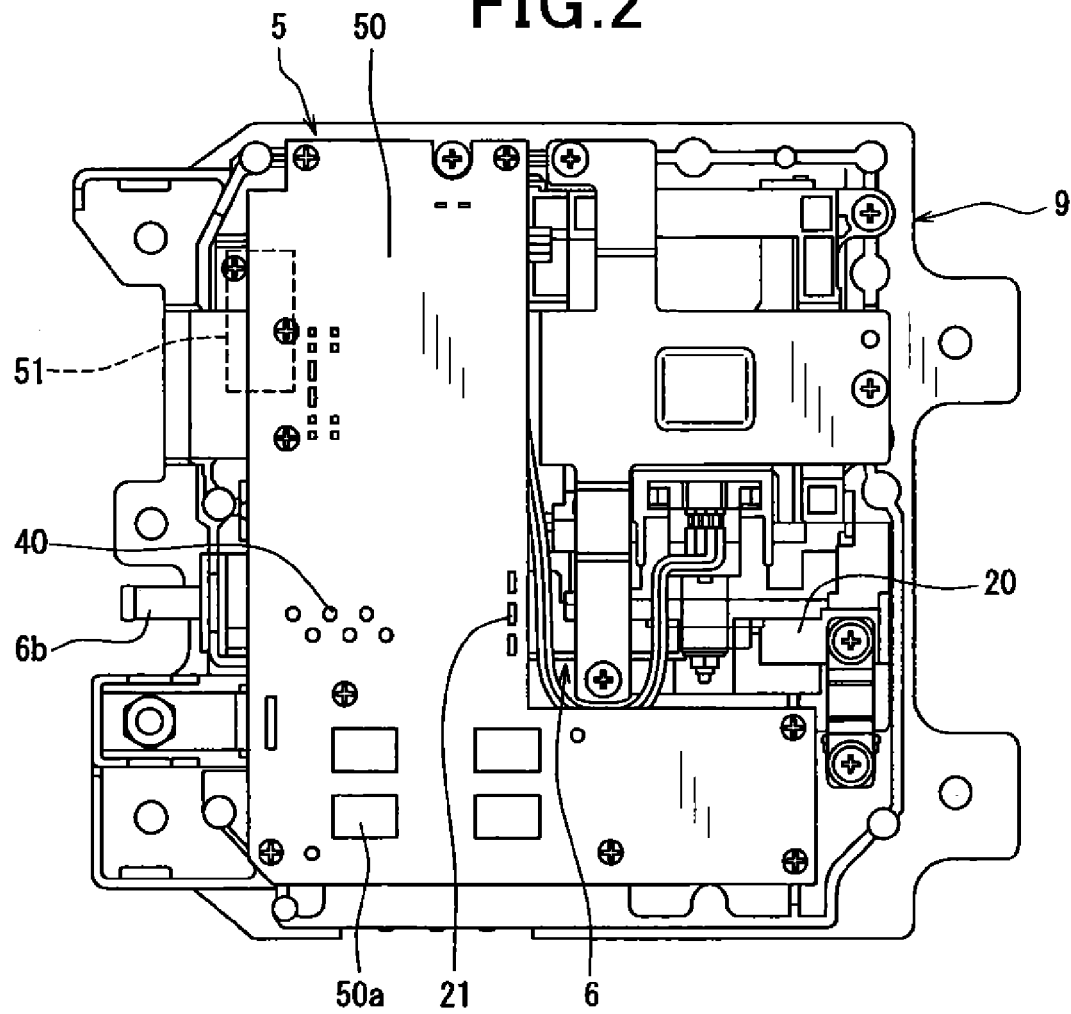
FIG. 2 is a planar view of the battery pack including the submergence detecting device according to the first embodiment, in a state in which a cover is removed.
Figure 3:
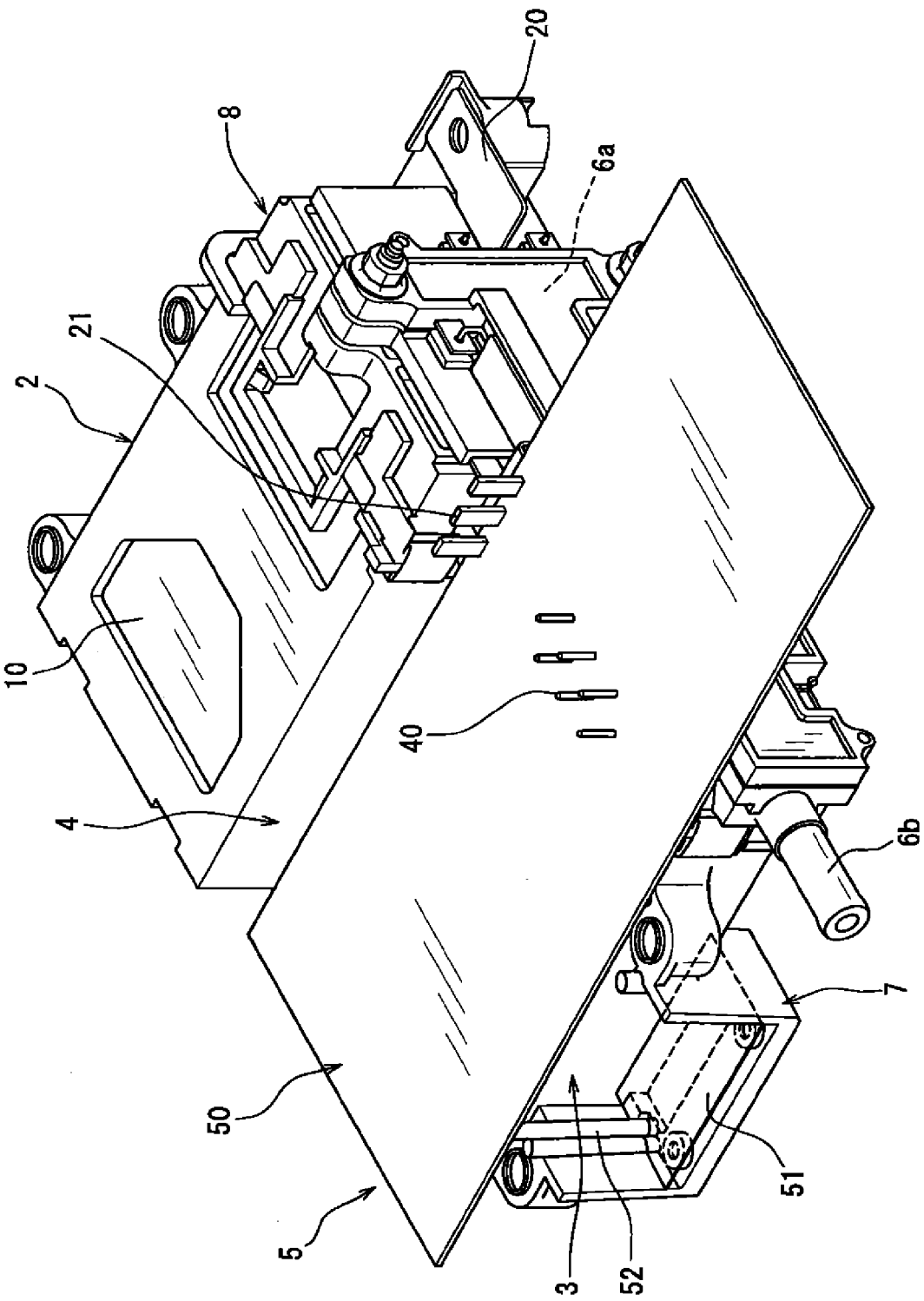
FIG. 3 is a perspective view of the battery pack including the submergence detecting device according to the first embodiment, in a state in which the cover and a base are removed.

As shown in FIG. 2 and FIG. 3, the sensor board 51 of the submergence detecting device 5 is supported from below by a base portion in an area positioned below and to the side of the second layer-built battery group 3. The base portion forms a portion of the battery case 7. The sensor board 51 is fitted onto the base portion and fixed by a screw or the like. A submergence detecting terminal 53 is provided in the sensor board 51. The submergence detecting terminal 53 detects a submerged state by coming into contact with water that has infiltrated the case and reached the base portion.

Figure 4:
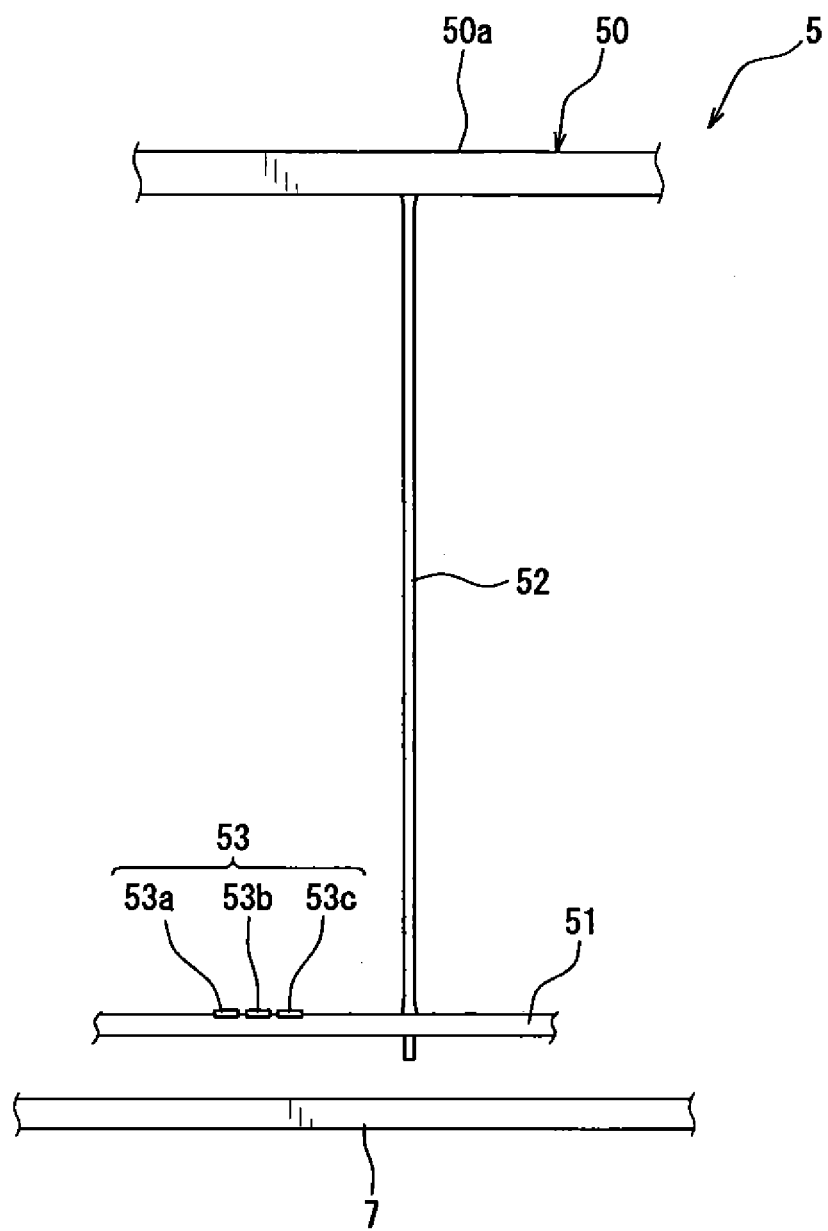
FIG. 4 is a front view of the submergence detecting device according to the first embodiment.

As shown in FIG. 4, the submergence detecting terminal 53 configures a detecting section of a submergence sensor. The submergence detecting terminal 53 is composed of three conductive sections 53a, 53b, and 53c. The conductive sections 53a, 53b, and 53c are formed as a conductor pattern electrode by printing or the like, such that the three conductive sections 53a, 53b, and 53c are aligned with space therebetween on the top surface of the sensor board 51. Each of the three conducting sections 53a, 53b, and 53c conducts to the communication line 52 communicating between the sensor board 51 and the control board 50, via copper wires placed on the sensor board 51. The communication line 52 extends upwards from the sensor board 51 and is connected to the submergence judging device mounted on the control substrate 50. Signals from each conductive section 53a, 53b, and 53c are outputted to the submergence judging device via the communication line 52.

In this way, the submergence detecting terminal 53 is disposed in a position away from the control board 50 mounted on the submergence judging device in the downward direction by a distance equivalent to the length of the communication line 52. In other words, the distance by which the submergence detection position is separated from the control board 50 is determined by the length of the communication line 52, or in other words, the positional relationship between the control board 50 and the submergence detecting terminal 53. Electronic components, such as a microcomputer, a connector, a thermistor, a fuse, a capacitor, a resistor, a diode, a transistor, and a timer, are mounted on the control board 50 that is positioned higher than the submergence detecting terminal 53.

When water infiltrates the case and reaches the base portion formed in the battery case 7, the sensor board 51 is gradually submerged. At this time, the sensor board 51 becomes wet, and an electrical resistance value between the conductive sections 53a, 53b, and 53c decreases. As a result the decrease being detected, the signal indicating a submerged state is outputted to the submergence judging device via the communication line 52. The submergence judging device transmits, to the battery control device, a fact that submergence has occurred. The battery control device stops charging the single cells 10, stops discharging to the outside, and the like, and performs notifying a user of the submerged state by a screen display, generation of alarm sound, or the like. Therefore, the user becomes aware that submergence has occurred. The user can terminate use of the battery, and take measures, if necessary, to stop further submergence or to ensure personal safety.

According to the first embodiment, the submergence detecting device 5 includes the submergence detecting terminal 53 and the submergence judging device. The submergence detecting terminal 53 is composed of at least two conductive sections 53a, 53b, and 53c disposed within the case. The submergence detecting terminal 53 detects the submerged state by coming into contact with water than has infiltrated the case from a predetermined area. The submergence judging device is disposed within the case. At least signals related to submergence detection are inputted into the submergence judging device from the submergence detecting terminal 53. The submergence judging device then judges whether submergence has occurred. The submergence detecting terminal 53 is disposed in a position away from the submergence judging device in the downward direction.

According to the configuration, the submergence detecting terminal 53 comes into contact with the water and detects infiltration of the water at a position away from the submergence judging device provided on the control board 50 in the downward direction. Water that has infiltrated into the case slowly collects and soon stagnates in the bottom portion within the case. As the result, each section may become completely submerged. However, the submergence detecting device 5 according to the first embodiment can detect the infiltration of water at an early stage, before the submergence judging device is submerged. Furthermore, when the submergence detecting device 5 detects the submerged state, measures to protect the submergence judging device, the single cells 10, and various electronic components from the water can be immediately taken. Therefore, the submergence detecting device 5 can detect the submerged state from a position away from the submergence judging device. As a result, measures required for the safety of the submergence judging device, the single cells 10, other electronic components, and the like can be taken with certainty.

In addition, the control board 50 that detects the state of the plurality of single cells 10 is disposed in the stepped space 4 provided in the battery pack 1. According to the configuration, the distance between the components mounted on the control board 50 and the single cells 10 can be shortened. As a result, electrical resistance between the components and the single cells 10 can be reduced. Furthermore, wires can be shortened as much as possible, and unnecessary complicated layouts for detecting the battery state can be avoided.

In addition, because the control board 50 is disposed in the stepped space 4, the distance between the submergence detecting terminal 53 that detects the water infiltrating the case and the control board 50 can be secured. In addition, the control board 50 can be stably disposed such as to be separated by a distance amounting to the layer height of the single cells 10 (the layer height of the second layer-built cell group 3). Furthermore, space for mounting the assembled battery and the control unit can be made compact. Hence the battery pack 1 may be mounted in spite of a narrow space to be mounted in a vehicle.

Second Embodiment

Figure 5:
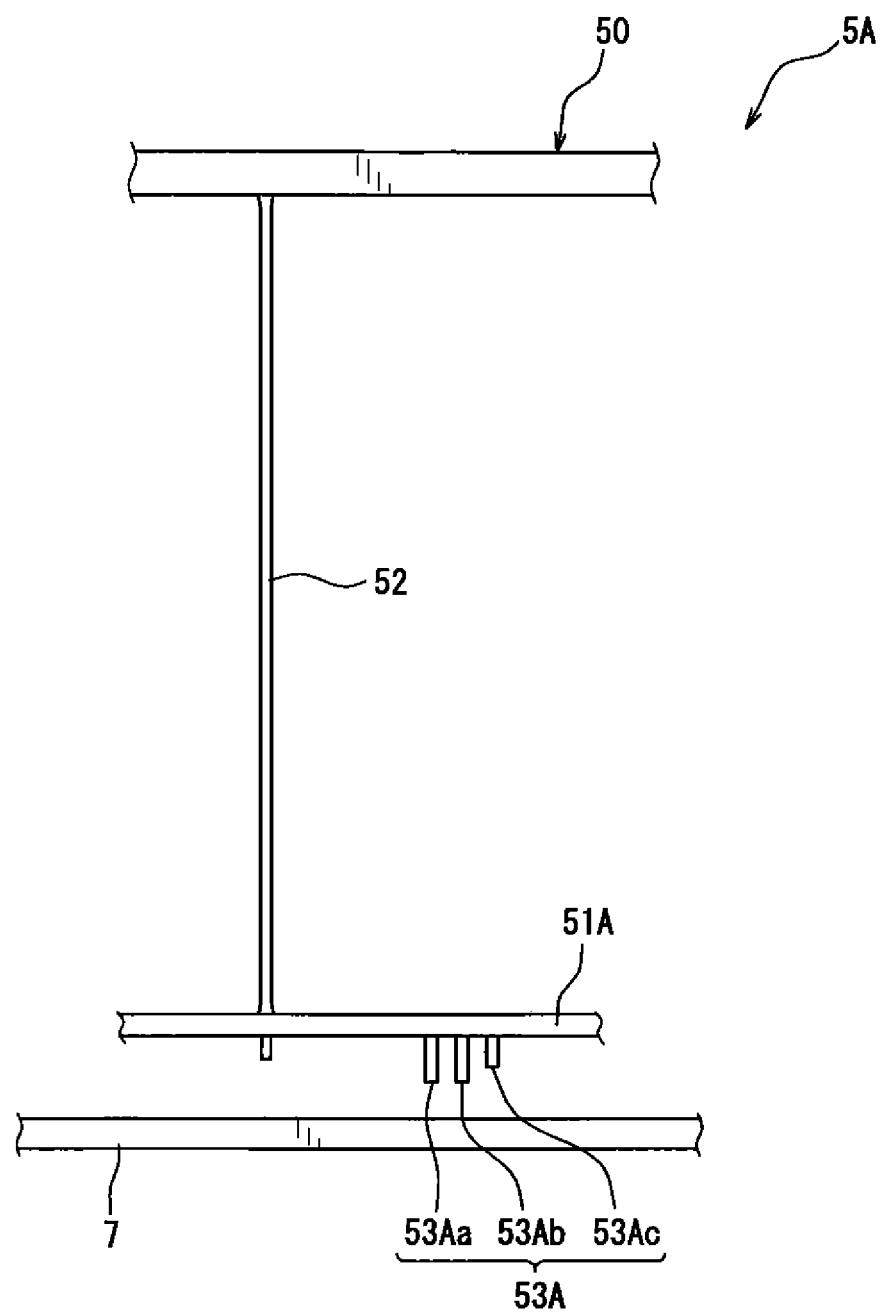
FIG. 5 is a front view of a submergence detecting device according to a second embodiment.

According to a second embodiment, a submergence detecting device 5A that is an embodiment differing from the first embodiment will be described with reference to FIG. 5. Constituent components having the same reference number as those in the drawings according to the first embodiment and configurations not described in the second embodiment are similar to those according to the first embodiment. Similar effects are achieved.

In the submergence detecting device 5A, an aspect of a submergence detecting terminal 53A differs from that of the submergence detecting device 5. As shown in FIG. 5, the submergence detecting terminal 53A included in the submergence detecting device 5A has three conductive sections 53Aa, 53Ab, and 53Ac. The first conductive section 53Aa, the second conductive section 53Ab, and the third conductive section 53Ac configure three terminal portions that are arrayed in order. The first conductive section 53Aa, the second conductive section 53Ab, and the third conductive section 53Ac are formed to project downwards from the underside of a sensor board 51A. Each of the three conductive sections 53Aa, 53Ab, and 53Ac conducts to the communication line 52 communicating between the sensor board 51A and the control board 50, via copper wires placed on the sensor board 51A.

The third conductive section 53Ac is disposed such as to be positioned above the first conductive section 53Aa and the second conductive section 53Ab. Furthermore, the first conductive section 53Aa and the second conductive section 53Ab are positioned such that the lower end positions are at the same height. Therefore, first conductive section 53Aa and the second conductive section 53Ab are submerged before the third conductive section 53Ac. In other words, the submergence detecting terminal 53A detects the water infiltrating the area that is a portion of the battery case 7 and opposing the sensor board 51A a plurality of times.

According to the second embodiment, the submergence detecting terminal 53A has at least three conductive sections 53Aa, 53Ab, and 53Ac. At least one conductive section 53Ac, among the three conductive sections 53Aa, 53Ab, and 53Ac, is disposed such that the lower end position is above those of the other conductive sections 53Aa and 53Ab.

As a result, the water that has infiltrated a portion of the battery case 7 opposing the sensor board 51A first comes into contact with the first conductive section 53Aa and the second conductive section 53Ab. The electrical resistance value between the first conductive section 53Aa and the second conductive section 53Ab decreases. The submergence judging device detects the decrease and outputs a signal indicating a first-stage submerged state to the battery control device. The battery control device can perform a measure against the first-stage submerged state. When water infiltration continues, the water wets the third conductive section 53Ac. The electrical resistance value between conductive sections including the third conductive section 52Ac decreases. The submergence judging device detects the decrease and outputs a signal indicating a second-stage submerged state to the battery control device. The battery control device can perform a measure against the second-stage submerged state. In this way, the submergence detecting device 5A can detect the submerged state in a plurality of stages. Therefore, as a result of the submergence detecting device 5A, the advancement of the submergence state can be known in a plurality of stages. A measure suitable for the known submergence state can be taken.

Third Embodiment

Figure 6:
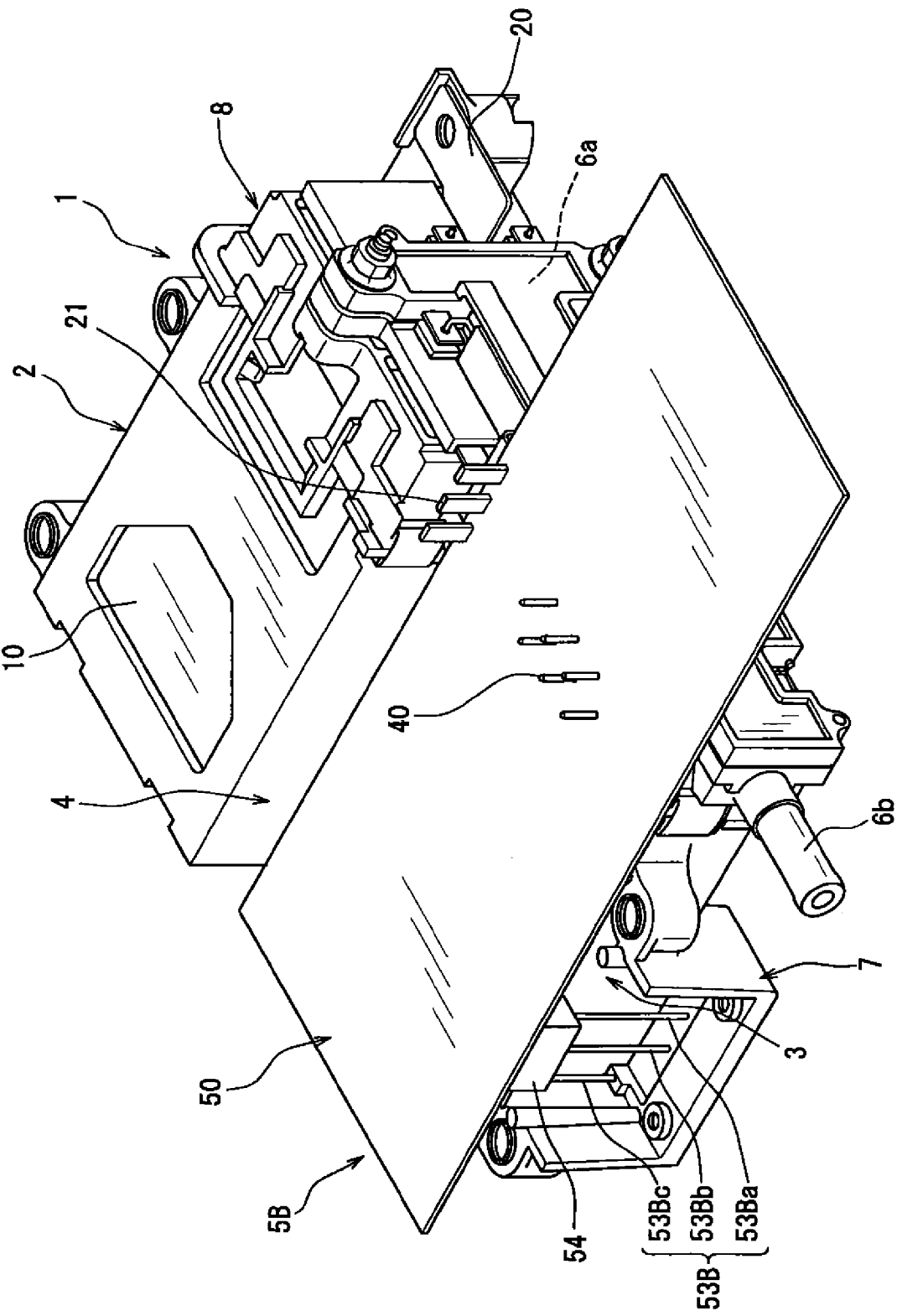
FIG. 6 is a perspective view of a battery pack including a submergence detecting device according to a third embodiment, in a state in which a cover and a base are removed.

According to a third embodiment, a submergence detecting device 5B that is an embodiment differing from the first embodiment will be described with reference to FIG. 6. Constituent components having the same reference number as those in the drawings according to the first embodiment and the second embodiment, and configurations not described in the third embodiment are similar to those according to the first embodiment. Similar effects are achieved.

In the submergence detecting device 5B, an aspect of a submergence detecting terminal 53B differs from that of the submergence detecting device 5. As shown in FIG. 6, the submergence detecting terminal 53B included in the submergence detecting device 5B has three conductive sections 53Ba, 53Bb, and 53Bc. The first conductive section 53Ba, the second conductive section 53Bb, and the third conductive section 53Bc configure three terminal portions that are arrayed in order. The first conductive section 53Ba, the second conductive section 53Bb, and the third conductive section 53Bc are formed to project downwards from the underside of the control board 50. Each of the three conductive sections 53Ba, 53Bb, and 53Bc conducts to the submergence judging device mounted on the control board 50, via copper wires placed on the control board 50. In other words, the three conductive sections 53Ba, 53Bb, and 53Bc are rod-shaped bodies. One end of each of the three conductive sections 53Ba, 53Bb, and 53Bc is joined to the control board 50 by soldering, welding, or the like. The other end is suspended towards a portion of the battery case 7.

Furthermore, the base section of each conductive section 53Ba, 53Bb, and 53Bc towards the control board 50 side is supported by a connector 54. The connector 54 is composed of a resin material. The connector 54 is molded such as to cover a portion of the submergence detecting terminal 53B. The connector 54 is fixed to the control board 50 by a single operation by an engaging means with an engagement between a tab portion and a hole portion.

The lower end position of the third conductive section 53Bc is disposed such as to be positioned above those of the first conductive section 53Ba and the second conductive section 53Bb. Furthermore, the first conductive section 53Ba and the second conductive section 53Bb are positioned such that the lower end positions are at the same height. Therefore, first conductive section 53Ba and the second conductive section 53Bb are submerged before the third conductive section 53Bc. In other words, the submergence detecting terminal 53B detects the water infiltrating the area that is a portion of the battery case 7 and positioned directly below the submergence detecting terminal 53B a plurality of times.

The submergence detecting device 5B according to the third embodiment includes a resin member (54E) that covers and insulates a portion of the submergence detecting terminal 53B. As a result, the position of the submergence detecting terminal 53B capable of detecting the submergence state can be set by selection of the area of the submergence detecting terminal 53B to be covered by the connector 54 that is a resin member. In other words, the area of the submergence detecting terminal 53B that is not covered by the connector 54 is set to the height at which detection of the submergence state is desired. The submergence detecting terminal 53B is covered by the connector 54 at the height where detection is not required. In this way, as a result of the submergence detecting device 5B, a product can be acquired that is capable of setting the detection position for the submergence state to an arbitrary height.

In addition, the submergence detecting terminal 53B according to the third embodiment achieves effects similar to those of the submergence detecting terminal 53A according to the second embodiment regarding detection of the submergence state.

Fourth Embodiment

Figure 7:
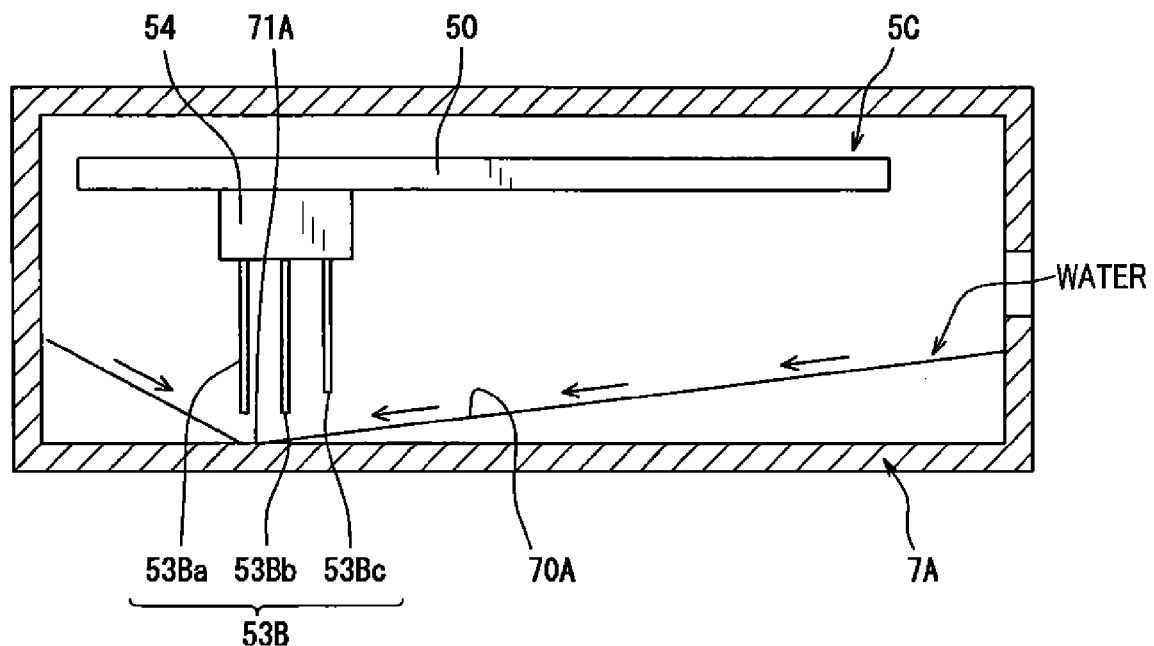
FIG. 7 is a cross-sectional view of a structure within a case of a submergence detecting device according to a fourth embodiment.

According to a fourth embodiment, a submergence detecting device 5C that is an embodiment differing from the third embodiment will be described with reference to FIG. 7. Constituent components having the same reference number as those in the drawings according to the first embodiment and the third embodiment, and configurations not described in the fourth embodiment are similar to those according to the above-described embodiments. Similar effects are achieved.

The submergence detecting device 5C differs from the submergence detecting device 5 in that a fluid guiding section 70A that guides the water is included. As shown in FIG. 7, the submergence detecting device 5C includes the fluid guiding section 70A that guides the water towards the bottom portion within a battery case 7A in the direction directly below the submergence detecting terminal 53B. The fluid guiding section 70A is a sloped bottom surface formed in the bottom portion within the battery case 7A. The fluid guiding section 70A forms a bottom surface that becomes lower towards the area of a collecting section 71A provided directly below the submergence detecting terminal 53B. In other words, the bottom surface position of the battery case 7A is such that the area equivalent to the collecting section 71A is the lowest.

According to the fourth embodiment, the fluid guiding section 70A is formed in the bottom portion within the battery case 7A. The fluid guiding section 70A guides the water towards the collecting section 71A positioned directly below the submergence detecting terminal 53B. According to the configuration, the water that has infiltrated the battery case 7A is collected in the collecting section 71A directly below the submergence detecting terminal 53B by way of the fluid guiding section 70A. As a result, the submergence state can be detected by the effect of water being collected, even when the amount of infiltrating water is still small. Therefore, submergence at an early stage can be detected, and early-stage safety measures and the like can be taken. In this way, the submergence detecting device 5C capable of detecting submergence at an early stage with certainty can be provided.

Fifth Embodiment

Figure 8:
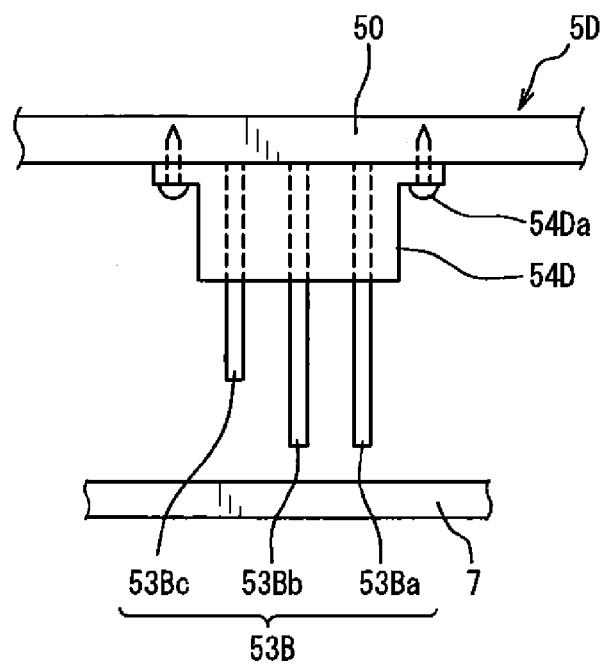
FIG. 8 is a front view of a submergence detecting terminal of a submergence detecting device according to a fifth embodiment.

According to a fifth embodiment, a submergence detecting device 5D that is an embodiment differing from the third embodiment will be described with reference to FIG. 8. Constituent components having the same reference number as those in the drawings according to the third embodiment, and configurations not described in the fifth embodiment are similar to those according to the third embodiment. Similar effects are achieved.

In the submergence detecting device 5D, a fixing structure of a connector 54D that is a resin member and the control board 50 differs from that of the submergence detecting device 5B. As shown in FIG. 8, the connector 54D included in the submergence detecting deice 5D supports the base portions on the control board 50 side of all conductive sections 53Ba, 53Bb, and 53Bc. The connector 54D is fixed to the control board 50 by a fastening means composed of a screw 54Da.

Sixth Embodiment

Figure 9:
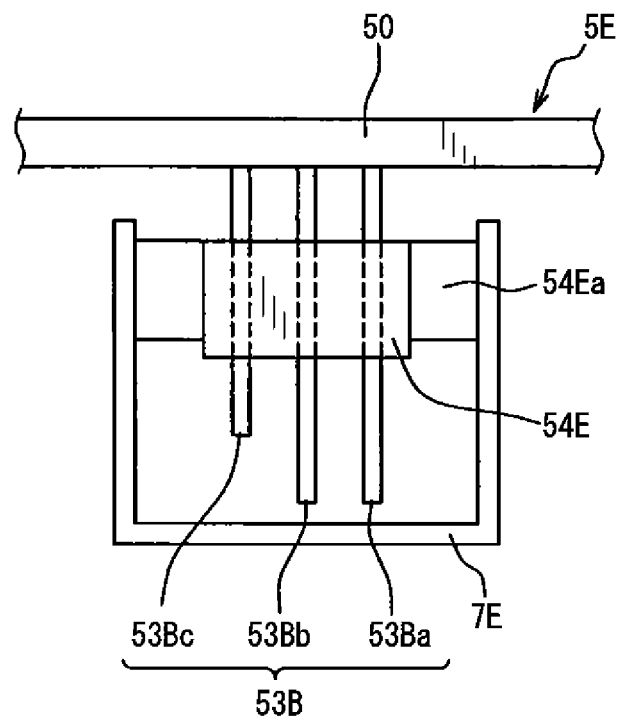
FIG. 9 is a front view of a submergence detecting terminal of a submergence detecting device according to a sixth embodiment.

According to a sixth embodiment, a submergence detecting device 5E that is an embodiment differing from the third, fourth, and fifth embodiments will be described with reference to FIG. 9. Constituent components having the same reference number as those in the drawings according to the above-described embodiments, and configurations not described in the sixth embodiment are similar to those according to the above-described embodiments. Similar effects are achieved.

In the submergence detecting device 5E, an aspect of a connector 54E that is molded to cover a portion of the submergence detecting terminal 53B differs from that in the submergence detecting device 5B. As shown in FIG. 9, the connector 54E does not support the base portions on the control board 50 side of all conductive sections 53Ba, 53Bb, and 53Bc. Rather, the connector 54E supports the intermediate portions thereof. Furthermore, the connector 54E is a member integrally configured with a portion of the battery case 7 or a portion of the smoke discharging duct 6.

According to the sixth embodiment, the submergence detecting device 5E is capable of adjusting the height at which submergence is detected by setting the area that is molded by the resin member. In this respect, effects similar to those of the submergence detecting device 5B according to the third embodiment can be achieved.

Furthermore, the connector 54E is provided integrally with a portion of the battery case 7 or smoke discharging duct 6. According to the configuration, the submergence detecting terminal 53B can be supported by a resin member that is integrated with the battery case 7. Therefore, force against the load applied to the water detecting terminal 53B can be provided. Damage to the submergence detecting terminal 53B can be prevented. Therefore, appropriate detection by the submergence detecting terminal 53B and long-term use can be actualized. Detection capability for the submergence state can be improved.

Other Embodiments

Preferred embodiments of the present invention are as described above. However, the present invention is not limited to the above-described embodiments. Various modifications can be made without departing from the spirit of the present invention. The structures according to the above-described embodiment are merely examples. The scope of the present invention is not limited to the described scope. The scope of the present invention is indicated by the expressions in the scope of claims, and includes meanings equivalent to the expressions in the scope of claims and all modifications within the scope.

The fluid guiding section 70A described in the above-described embodiments is configured by a sloped bottom surface that becomes lower towards the collecting section 71A directly below the submergence detecting terminal 53B. In addition, the fluid guiding section 70A may be configured by a groove section provided on the bottom surface of the battery case 7. Furthermore, the fluid guiding section 70A may be that in which a shape using capillary phenomenon is formed on the bottom surface of the battery case 7.

According to the above-described embodiments, a groove section that extends downward may be formed on the surface of the connector 54, 54D, and 54E that supports the submergence detecting terminal. The groove section enables water attached to the surface of the connector 54, 54D, and 54E to drip downward along the groove section.

The assembled battery described according to the above-described embodiments has the stepped space 4 amounting to approximately one single cell 10 formed by the two layer-built cell groups 2 and 3 being aligned in the horizontal direction. However, the stepped space 4 is not limited to that amounting to approximately one single cell 10. For example, the stepped space included in the present invention may be of a size allowing approximately two or more single cells 10 to be aligned in the horizontal direction. Alternatively the stepped space may be of a size amounting to approximately two or more single cells 10 in the thickness direction of the single cell 10. In addition, the assembled battery includes an aspect having a plurality of stepped spaces having differing lengths in the thickness direction.

According to the above-described embodiments, the assembled battery is placed in a position such that the thickness direction (layering direction) of the single cell 10 is in the up/down direction. However, the placement position of the assembled battery of the present invention is not limited to this direction. For example, the assembled battery may be placed such that the electrode terminal of each single cell 10 projects upwards from the exterior package.

According to the above-described embodiments, the battery case 7 and the insulating cover 8 are members separated from each other. However, the present invention is not limited thereto. The battery case 7 and the insulating cover 8 may be configured as a single member.

What is claimed is:

1. A submergence detecting device, comprising:
   a submergence detecting terminal which is composed of at least two conductive sections disposed within a case and detects a submergence state at a predetermined area within the case;
   a control board on which a submergence judging device disposed within the case is mounted, the submergence judging device being configured to receive at least a signal relating to submergence detection from the submergence detecting terminal and judge whether or not submergence has occurred; and
   a resin member that covers and insulates a portion of the submergence detecting terminal, wherein
   the submergence detecting terminal is disposed in a position away from the submergence judging device, mounted on the control board, in a downward direction,
   the submergence detecting terminal is supported by the resin member,
   the resin member is supported by a wall of the case, and
   the resin member is disposed in a position spaced apart from the control board.

2. The submergence detecting device according to claim 1, wherein the submergence detecting terminal has at least three conductive sections, wherein a lowest position of one of the conductive sections is disposed higher up than that of others of the conductive sections.

3. The submergence detecting device according to claim 1, further comprising a fluid guiding section provided in a bottom portion within the case so as to guide fluid which has infiltrated into the case to an area directly below the submergence detecting terminal.

4. The submergence detecting device according to claim 2, further comprising a fluid guiding section provided in a bottom portion within the case so as to guide fluid which has infiltrated into the case to an area directly below the submergence detecting terminal.

5. The submergence detecting device according to claim 1, wherein the submergence detecting terminal is mounted away from the control board.

6. The submergence detecting device according to claim 1, further comprising a sensor board on which the submergence detecting terminal is mounted, the sensor board being separate from the control board and mounted below the control board in the downward direction.

* * * * *